United States Patent [19]

Skeldon

[11] Patent Number: 4,571,077

[45] Date of Patent: Feb. 18, 1986

[54] LASER-TESTING SCATTERFEROMETER

[75] Inventor: Mark D. Skeldon, Rochester, N.Y.

[73] Assignee: The United States of America as represented by the Secretary of the Army, Washington, D.C.

[21] Appl. No.: 574,220

[22] Filed: Jan. 26, 1984

[51] Int. Cl.⁴ .............................................. G01B 9/02
[52] U.S. Cl. ................................. 356/239; 356/35.5; 356/345; 356/339
[58] Field of Search ...................... 356/35.5, 338, 339, 356/342, 345, 239

[56] References Cited

U.S. PATENT DOCUMENTS

| | | | |
|---|---|---|---|
| 3,892,494 | 7/1975 | Baker et al. | 356/239 |
| 4,056,323 | 11/1977 | Ludman | 356/106 R |
| 4,269,518 | 5/1981 | Rahn | 356/445 |
| 4,310,242 | 1/1982 | Genco et al. | 356/128 |

Primary Examiner—John E. Kittle
Attorney, Agent, or Firm—Max L. Harwell; Aubrey J. Dunn; Anthony T. Lane

[57] ABSTRACT

In order to test a laser rod for inclusions, which the usual interferometer does not test, one of the interferometer mirrors is placed on a lens such that light scattered from inclusions in the rod passes through the lens to a detector.

3 Claims, 1 Drawing Figure

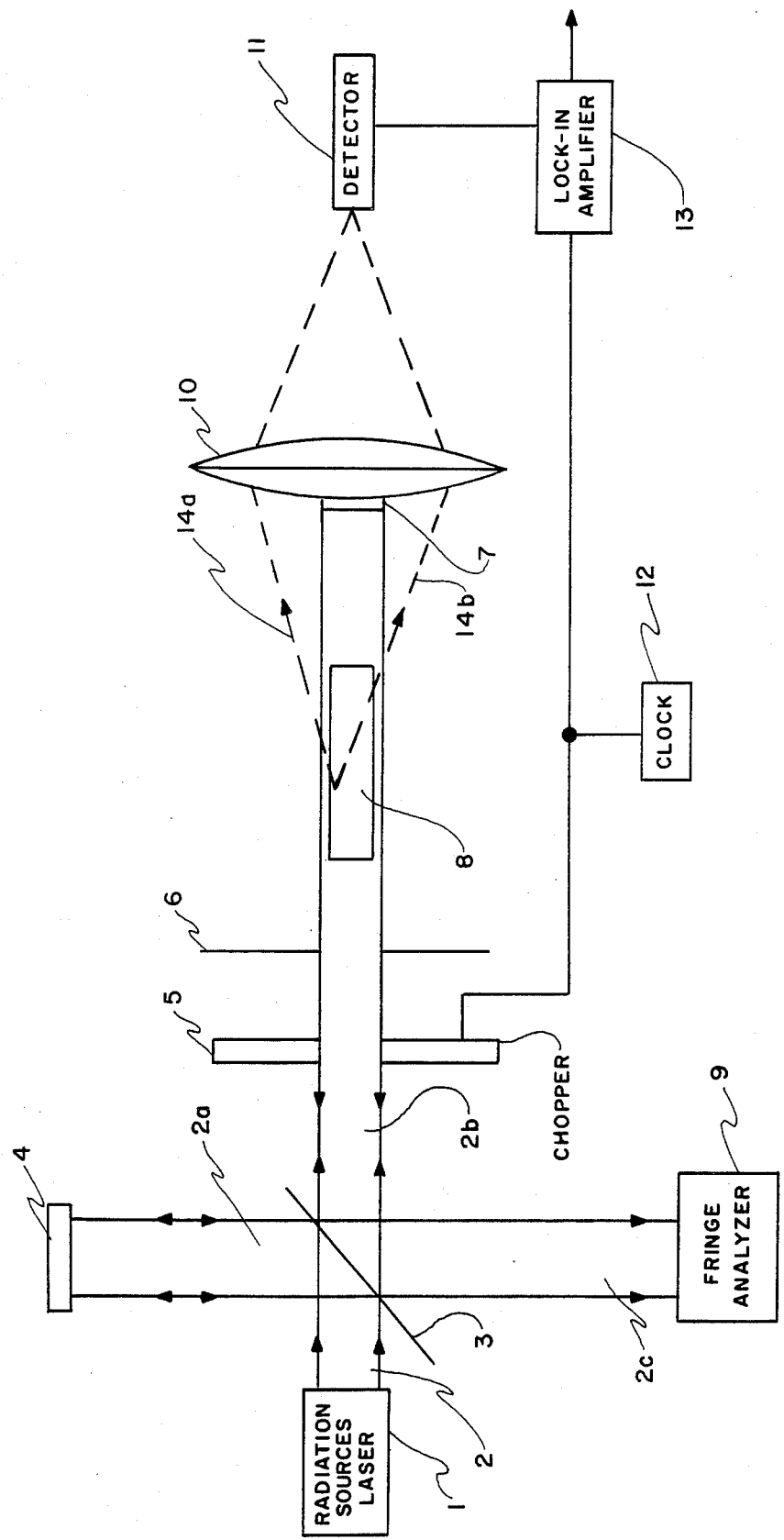

LASER-TESTING SCATTERFEROMETER

The invention described herein may be manufactured, used, and licensed by the U.S. Government for governmental purposes without the payment of any royalties thereon.

BACKGROUND OF THE INVENTION

This invention is in the field of laser-testing interferometers. In the manufacture of solid laser rods (specifically, Nd: YAG), it has been found that about half of the material from which the rods is made is unusable because of inclusions in the material. Visual inspection techniques weed out gross inclusions, but obviously do not detect microscopic ones. After a rod is cut from a section of crystal boule with no visible inclusions, it is tested with an interferometer for internal strain, end face flatness, and perpendicularity to the crystal axis. Unfortunately, this test does not detect microscopic inclusions; these inclusions cause scattering in the forward laser beam direction. The instant invention is a modification or improvement to an interferometer whereby these inclusions may be detected.

SUMMARY OF THE INVENTION

The invention is an improved interferometer (scatterferometer) for testing laser rods wherein a normally plane mirror in the interferometer is replaced by a plane mirror spot on the center of a lens. With this arrangement, the interferometer can not only test the rod for internal strain, end face flatness, and perpendicularity of the crystal axis, but, by use of a radiation detector beyond the lens, can detect microscopic inclusions in the crystal. The inclusions cause forward scattering of the interferometer radiation in the rod, and the scattered radiaiton passes around the mirror spot on the lens, through the lens, and falls onto the radiation detector.

BRIEF DESCRIPTION OF THE DRAWINGS

The single drawing FIGURE shows a schematic diagram of an scatterferometer made in accordance with the invention.

DETAILED DESCRIPTION OF THE PREFERRED EMBODIMENT

The invention may be best understood when this description is taken in conjunction with the drawings. In the single drawing FIGURE, reference numeral 1 designates a laser radiation source which provides a test beam for the scatterferometer. Beam 2 from source 1 is directed onto beam-splitter 3 and is split thereby into beams 2a and 2b. Beam 2a is retroreflected by mirror 4 and a portion passes through beam splitter 3 as a portion of beam 2c. Beam 2a passes through chopper 5 and aperture 6 to mirror 7, from which it is retroreflected back to beam splitter 3, and partially reflects as a portion of beam 2c. The laser rod under test is designated 8 and is in beam 2b. Beam 2c, which is the combination of retroreflected beams 2a and 2b, passes to fringe analyzer 9. Thus far, with the exception of chopper 5 and aperture 6, all of the recited elements are well known in laser testing interferometers. Besides chopper 5 and aperture 6, whose functions will be explained shortly, lens 10, detector 11, clock 12, and lock-in amplifier 13 are added to make a scatterferometer. Aperture 6 has an opening congruent to mirror 7 such that, for a perfect laser rod under test, all of beam 2b will be retroreflected. For a laser rod with inclusions, beam 2b will be partially scattered around mirror 7, as shown by rays 14a and 14b. Chopper 5, which may be mechanical or electro-optical, is operated by pulses from the source 5 of clock pulses; these pulses also are applied to lock-in amplifier 13. The output of detector 11 is applied as an input to amplifier 13 and the output of 13 is thus directly related to the number and size of any inclusions in rod 8. In order to obtain a quantized scattering indication, the output (from 13) with the laser rod in place and chopper 5 operating may be compared to the output of 13 with the rod removed (and the chopper operating).

While a specific embodiment of the invention has been shown and described, other embodiments may be obvious to one skilled in the art, in light of this disclosure. For example, an antireflection coating may be applied to lens 10 and/or a filter to pass only the source laser wavelength may be between the lens and detector 11.

Although its shape is not critical, the preferred shape of mirror 7 is circular, and the opening of aperture 6 will likewise be circular. Mirror 7 may take the form of a flat metal disk glued to a flat portion on lens 10, or may be a metal surface applied to such a flat portion, or various other forms.

I claim:

1. A scatterferometer which is an improvement on an interferometer, wherein the interferometer includes: a laser radiation source for providing a test beam, a beam splitter for directing a first portion of said beam to a first retroreflector and a second portion of the beam to a second retroreflector, whereby a test laser rod is inserted into said second portion of said beam, and whereby said first and second portions of said beam partially recombine as a result of being reflected from said retroreflector, to give a fringe pattern in accordance with imperfections in said test rod, the improvement comprising:
   said second retroreflector is made as a highly reflective spot in the center of a positive lens;
   a chopper inserted in said second portion of said laser beam;
   an aperture for said second portion of said laser beam, between said chopper and said test laser rod; and
   a laser radiation detector on the opposite side of said lens from said spot.

2. The scatterferometer as set forth in claim 1 wherein said aperture is congruent to said spot.

3. The scatterferometer as set forth in claim 2 wherein said spot is flat.

* * * * *